(12) United States Patent
Rand

(10) Patent No.: US 7,089,935 B1
(45) Date of Patent: Aug. 15, 2006

(54) INHALATION DEVICE

(75) Inventor: Paul Kenneth Rand, Ware (GB)

(73) Assignee: Glaxo Group Limited, Greenford (GB)

( * ) Notice: Subject to any disclaimer, the term of this patent is extended or adjusted under 35 U.S.C. 154(b) by 0 days.

(21) Appl. No.: 09/889,751

(22) PCT Filed: Dec. 8, 1999

(86) PCT No.: PCT/EP99/09614

§ 371 (c)(1),
(2), (4) Date: Jul. 20, 2001

(87) PCT Pub. No.: WO00/43059

PCT Pub. Date: Jul. 27, 2000

(30) Foreign Application Priority Data

Jan. 22, 1999 (GB) .................................. 9901282.5
Feb. 16, 1999 (GB) .................................. 9903342.5

(51) Int. Cl.
*A61M 15/00* (2006.01)
(52) U.S. Cl. .............................. 128/203.15; 128/203.21
(58) Field of Classification Search ........... 128/203.12, 128/203.15, 203.21, 203.23, 205.21; 206/461, 206/471, 828
See application file for complete search history.

(56) References Cited

U.S. PATENT DOCUMENTS

| | | | |
|---|---|---|---|
| 3,654,890 A * | 4/1972 | Rigney et al. .............. | 116/308 |
| 5,590,645 A * | 1/1997 | Davies et al. ........... | 128/203.15 |
| 5,619,984 A | 4/1997 | Hodson et al. ........ | 128/203.15 |
| 5,694,920 A * | 12/1997 | Abrams et al. ........ | 128/200.16 |
| 5,709,202 A | 1/1998 | Lloyd et al. ........... | 128/200.14 |
| 6,032,666 A * | 3/2000 | Davies et al. ........... | 128/203.15 |
| 6,378,519 B1 * | 4/2002 | Davies et al. ........... | 128/203.21 |
| 6,536,427 B1 * | 3/2003 | Davies et al. ........... | 128/203.15 |
| 6,679,254 B1 * | 1/2004 | Rand et al. ............. | 128/203.15 |

FOREIGN PATENT DOCUMENTS

| | | |
|---|---|---|
| DE | 3823535 A | 1/1990 |
| EP | 0469814 A1 * | 2/1992 |
| GB | 2242134 A * | 9/1991 |
| WO | WO9516483 A | 6/1995 |
| WO | WO9737693 A | 10/1997 |

* cited by examiner

*Primary Examiner*—Teena Mitchell
(74) *Attorney, Agent, or Firm*—James P. Riek

(57) ABSTRACT

A medicament cartridge for use in an inhalation device comprising a carrier having a plurality of medicament retainers in a spiral path arrangement. Typically, the carrier is substantially planar. In one embodiment the carrier comprises an elongate carrier storable in a flat spiral configuration and extendable as a helix. There is also provided an inhalation device comprising a housing having an air inlet, an air outlet, an airway therebetween and a medicament carrier having a plurality of medicament retainers in a spiral path arrangement. A mover is provided for moving the medicament carrier relative to the housing so as to bring successive medicament retainers individually into communication with the airway.

22 Claims, 8 Drawing Sheets

INHALATION DEVICE

This application is filed pursuant to 35 U.S.C. §371 as a United States National Phase Application of International Application No. PCT/EP99/09614 filed 8 Dec. 1999, which claims priority from GB9901282.5 filed 22 Jan. 1999 in the United Kingdom and GB9903342.5 filed 16 Feb. 1999 in the United Kingdom The present invention relates to a medicament cartridge for an inhalation device for use in the administration of medicament to a patient. The cartridge has a plurality of medicament retainers in a spiral path arrangement.

The use of inhalation devices in the administration of medicaments, for example in bronchodilation therapy, is well known. Such devices generally comprise a body or housing within which a medicament container is located. A mouthpiece (or nozzle) is typically provided, wherein 'in use' the mouthpiece communicates with the medicament container to allow passage of medicament from the source to the mouthpiece and thence, to the patient.

In a typical dispensing operation the body of the device is held by the patient and the mouthpiece (or nozzle) of the inhalation device is placed in the mouth (or nose) of the patient. The patient inhales, thereby causing transfer of medicament from the medicament container to the interior of the body of the patient.

It is desirable that the inhalation device is able to provide a plurality of doses of medicament. Known devices include metered dose inhalers having an aerosol container comprising sufficient medicament to provide plural individual doses. Also known are dry powder inhalers having a reservoir of dry powder from which individual doses may be delivered.

Other known devices have a medicament carrier having plural individual medicament retainers thereon. One such carrier is shaped in the form of a rigid disc having plural medicament-containing blisters arranged in a circular configuration thereon. Typically, such discs are designed to provide from five to ten doses. Another such carrier has an elongate tape carrier having plural medicament-containing blisters arranged in a line along the length of the tape. The tape is generally retained on a spindle and the tape is progressively unwound from the spindle to allow access to individual blisters. Typically, such tape carriers are designed to provide about forty to sixty doses.

There is continuing interest in the design of medicament cartridges capable of providing very large numbers of individual doses. However, there is also a desire to reduce the size of the device, and hence the cartridge, so that it is readily portable by the patient. It will be appreciated that with the above described known carriers increasing the number of doses will also result in an inevitable and undesirable increase in the required size of disc and tape-winding on the spindle.

The Applicants have found that the use of a medicament cartridge comprising a carrier having a plurality of individually accessible medicament retainers in a spiral path arrangement allows for the provision of large numbers of doses from a single cartridge, whilst enabling the size of the cartridge to be kept at an acceptable level.

The Applicants have also found that the use of a medicament carrier comprising an elongate carrier having a plurality of individually accessible medicament retainers, wherein the carrier is storable in a flat spiral configuration and extendable for dispensing as a helix, allows for the provision of large numbers of doses from a single carrier, whilst enabling the size of the carrier and device to be kept at an acceptable level.

WO95/16483 describes an inhalation device comprising a housing, which houses a cylindrical container. The container has a number of helically arranged compartments, each of which contains a dose of powdered medicament. To allow for dosing of medicament, the container is rotated thereby bringing a compartment into communication with an airway. The airway communicates with an air inlet through which the patient inhales, which inhalation causing passage of medicament from the compartment through the airway to the air inlet.

According to one aspect of the present invention there is provided a medicament cartridge for use in an inhalation device comprising a carrier having a plurality of medicament retainers in a spiral path arrangement. The spiral path is preferably a flat (i.e. two-dimensional) spiral path.

The carrier may be formed from any suitable material including plastic materials. Preferably, the carrier is substantially planar. More preferably, the carrier is substantially rigid. Preferably, the carrier is circular in shape and is rotationally mountable.

The medicament retainers are sized and shaped for retention of medicament. Each retainer may, for example, be a medicament-retaining pocket. Suitable pocket forms include a cavity (recess) provided in the retainer, a cup having sidewalls standing proud from the carrier and any composite of these cavity/cup forms. A cover, preferably a hermetically sealing cover may be provided to the pocket.

In one preferred aspect, each medicament retainer comprises a pocket in the carrier. Preferably, a seal is provided to each pocket. In a particularly preferred aspect, the seal comprises a sealing tape arranged along said spiral path and each pocket is accessible by progressive removal of the tape from the spiral path.

In another preferred aspect, each medicament retainer comprises a hole in the carrier. Each hole may be provided with a mesh for retention of medicament. The mesh may be formed of any suitable materials including plastic materials. Covers, preferably hermetically sealing covers may be provided to seal the hole.

In a further aspect, the carrier is elongate, storable in a flat spiral configuration and extendable as a helix. Preferably, the medicament retainers are serially arranged along the elongate carrier. The elongate carrier is, for example a tape carrier.

Preferably, each medicament retainer comprises a cavity in the elongate carrier. Typically, a seal is provided to each cavity. More preferably the seal comprises a sealing tape and each cavity is individually accessible by peelable removal of the sealing tape.

The medicament retainers are sized and shaped for retention of medicament. Each retainer may, for example, be a medicament-retaining pocket. Suitable pocket forms include a cavity (recess) provided in the retainer, a cup having sidewalls standing proud from the carrier and any composite of these cavity/cup forms. A cover, preferably a hermetically sealing cover, may be provided to the pocket.

Preferably, each medicament retainer is sized to retain a single dose of medicament. More preferably, the medicament carrier has from 60 to 500, preferably from 100 to 300, medicament retainers.

The medicament doses may be applied to the carrier by any suitable method including wet and dry printing methods. Suitable wet printing methods include ink jet printing. Suitable dry printing methods include xerographic and electrostatic printing methods.

In use one or more of the medicament retainers are charged with medicament. In one aspect, there is provided a medicament cartridge comprising a carrier having a plurality of medicament doses thereon, wherein said doses are in a spiral path arrangement.

In another aspect, there is provided a medicament carrier for use in an inhalation device comprising an elongate carrier having a plurality of medicament doses thereon, wherein said elongate carrier is storable in a flat spiral configuration and extendable as a helix.

According to another aspect of the present invention there is provided an inhalation device comprising a housing having an air inlet, an air outlet and an airway therebetween;

a medicament carrier having a plurality of medicament retainers in a spiral path arrangement; and a mover for moving the medicament carrier relative to the housing so as to bring successive medicament retainers individually into communication with the airway.

Preferably, the medicament carrier is a substantially rigid circular disc, which is rotatable relative to the housing.

In one aspect, the circumference of the circular disc is provided with teeth and said teeth engage a worm drive for drivable rotation of the disc.

In one aspect, each medicament retainer comprises a pocket in a first face of the disc. Preferably, the second face of the disc has a spiral track for receipt of a tracking pin fixedly mounted on the housing such that as the disc rotates relative to the housing the tracking pin moves along the spiral track and the disc moves translationally relative to the housing.

According to a yet further aspect of the present invention there is provided an inhalation device comprising a housing having an air inlet, an air outlet and an airway therebetween;

a medicament carrier having a plurality of medicament retainers in a spiral path arrangement, each medicament retainer having a seal;

an actuator for progressively unsealing each medicament retainer on the spiral path.

Preferably, the device additionally comprises a mover for moving the medicament carrier relative to the housing so as to bring successive medicament retainers individually into communication with the airway.

Preferably, each medicament retainer comprises a pocket.

Preferably, said seal comprises a sealing tape arranged along said spiral path and wherein each pocket is serially accessible by peelable removal of the tape.

Preferably, an end of said sealing tape connects to said actuator and peelable removal of the sealing tape is achievable by movement of the actuator.

In one aspect, the actuator is rotatable relative to the housing such that rotation of the actuator results in coiling of the tape around the actuator. Preferably, the actuator is an axially mounted tapered pole.

According to a further aspect of the present invention there is provided an inhalation device comprising a housing having an air inlet, an air outlet and an airway therebetween;

an elongate carrier having a plurality of medicament retainers, wherein said elongate carrier is storable in a flat spiral configuration; and a mover in communication with the elongate carrier for helically extending the elongate carrier such as to successively move each medicament retainer to an access position.

Preferably, each medicament retainer comprises a cavity in the elongate carrier.

Preferably, each medicament retainer has a seal, the device additionally comprising an actuator for unsealing a medicament retainer at the access position.

In one aspect, the seal comprises a sealing tape arranged along the elongate carrier and wherein each successive cavity is accessible by peelable removal of the tape from the elongate carrier. More preferably, an end of said sealing tape connects to the actuator and peelable removal of the sealing tape is achievable by movement of the actuator relative to the elongate carrier.

Preferably, the mover is rotatable relative to the housing such that rotation of the mover results in coiling of the elongate carrier around the mover, and also said actuator is rotatable relative to the housing such that rotation of the actuator results in coiling of the tape around the actuator.

Preferably, the mover is an axially mounted tapered pole and the actuator is also an axially mounted tapered pole.

In another aspect, the actuator comprises a piercer for piercably unsealing a medicament retainer.

According to a still further aspect of the present invention there is provided an inhalation device comprising a housing having an air inlet, an air outlet and an airway therebetween;

an elongate carrier having a plurality of doses thereon, wherein said elongate carrier is storable in a flat spiral configuration; and a mover in communication with the elongate carrier for helically extending the elongate carrier such as to serially move each dose to an access position.

Preferably, the air outlet is provided with a mouthpiece. Herein the term 'mouthpiece' is used in a generic sense to mean an element shaped such as to be insertable into the mouth or nose of a patient for inhalation therethrough.

Preferably, the device is provided with a dose counter, which indicates the number of doses dispensed from or remaining in the container. More preferably, the dose counter comprises an indexing mechanism actuated by a predetermined movement of the medicament container relative to the body.

Preferably, the medicament is in dry-powder form.

According to a still further aspect of the present invention there is provided the use of an inhalation device as described herein for the administration of medicament to a patient.

Preferred embodiments of the present invention will now be described with reference to the accompanying drawings in which:

FIG. 1b is a view of the reverse medicament cartridge of FIG. 1a;

Figure 1A:
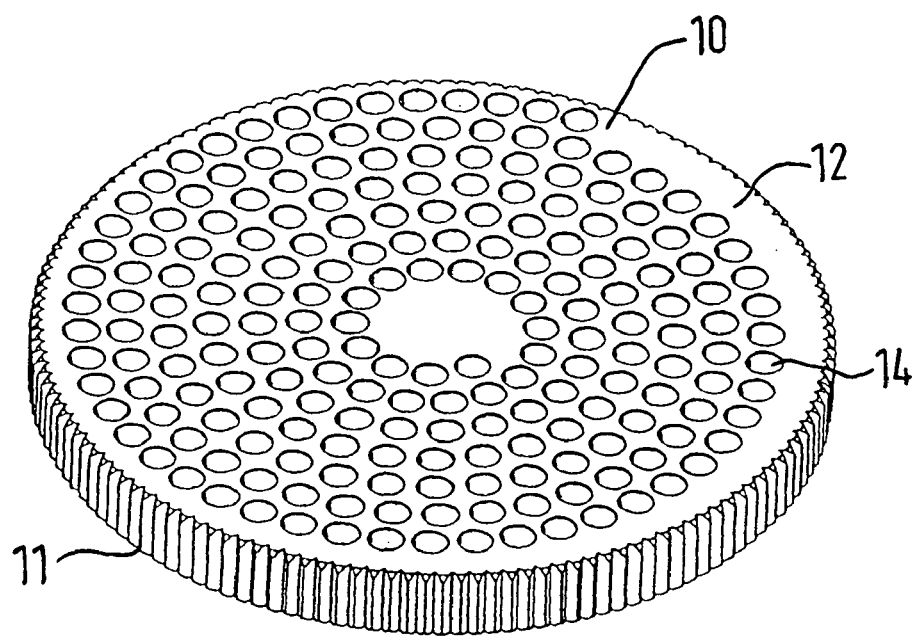
FIG. 1a is a view of the top a medicament cartridge in accord with the present invention.
Figure 1B:
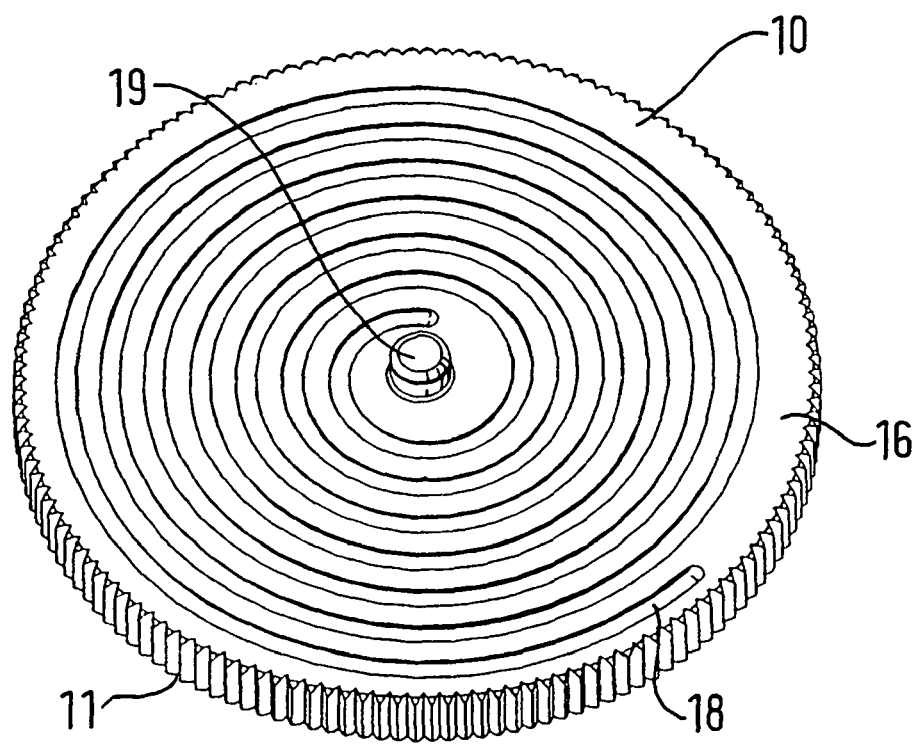

FIGS. 1a and 1b show a medicament cartridge in the form of a rigid disc 10 having teeth 11 on the circumference thereof. The top face 12 of the disc 10 is provided with a plurality of medicament retaining cavities 14 in a spiral path arrangement. The reverse face 16 of the disc 10 is provided with a spiral tracking groove 18 and a centrally located peg 19 to enable the disc to be mounted for rotation.

Figure 2:
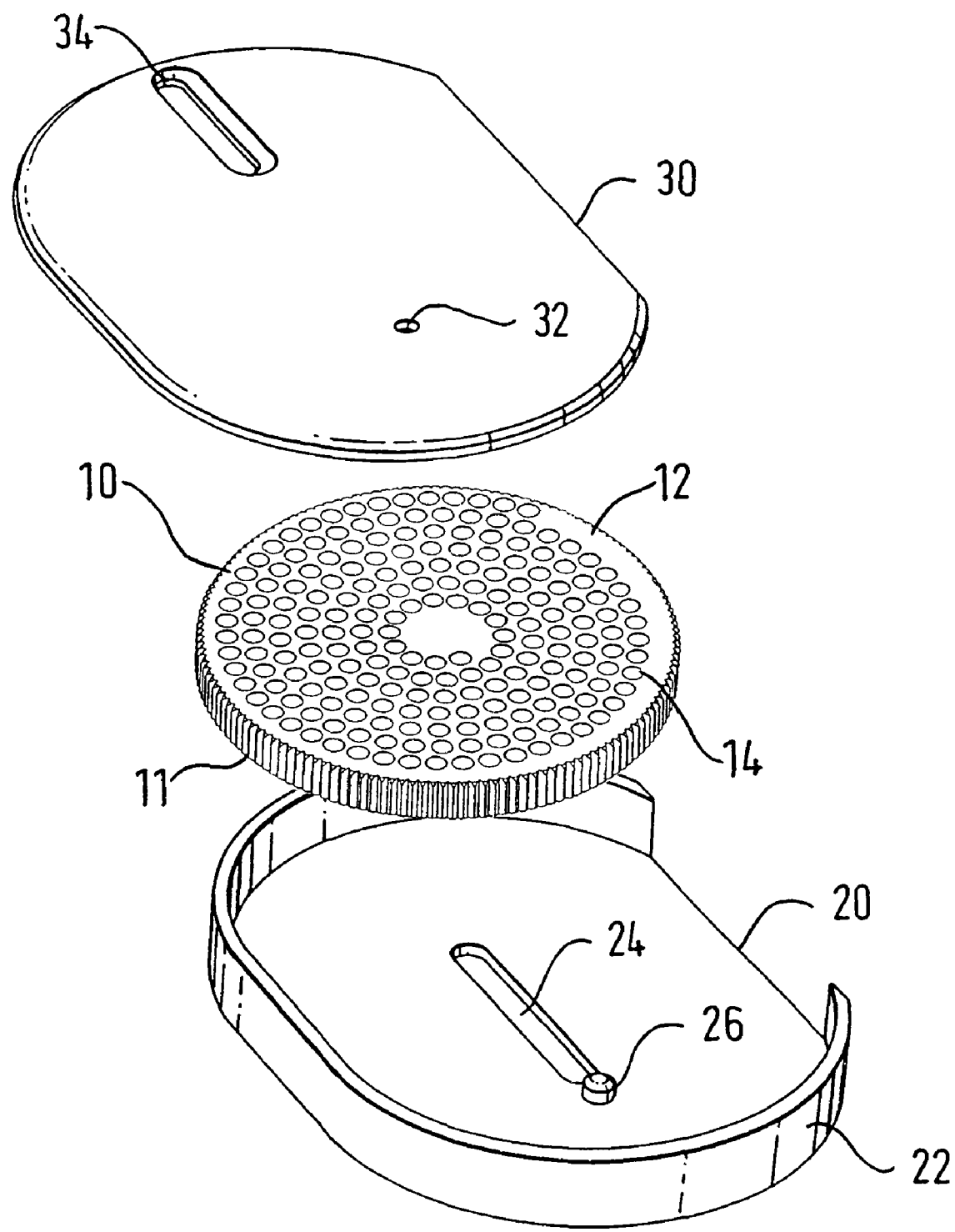
FIG. 2 is an exploded view of a cassette incorporating the medicament cartridge of FIG. 1a and 1b.

FIG. 2. shows an exploded view of a cassette incorporating the medicament cartridge of FIGS. 1a and 1b. The cassette has a bottom cover 20 having peripheral walls 22 extending partially therearound. The bottom cover 20 is provided with a slit 24 for receipt of the peg 19 on the reverse face 16 of the disc 10. The bottom cover 20 is also provided with a tracking pin 26, which is located adjacent to a first end of the slit 24. When the cassette is in assembled form the tracking pin 26 follows the spiral tracking groove 18 on the reverse face 16 of the disc cartridge 10. The top cover 30 of the cassette is provided with an exit hole 32 located to register with successive medicament retaining cavities 14 on the top face 12 of the disc 10. The top cover 30 is also provided with a window 34.

To enable access to successive medicament retainers (doses) in use, it may be understood that the disc 10 will be rotated to bring each successive medicament-retaining cavity 14 into registration with the exit hole 32. The tracking pin 26 will follow the spiral tracking groove 18 thereby causing the disc 10 to be translationally shifted in a direction set by the slit 24 in the bottom cover 20 of the cassette. The view through the window 34 may thus be used as an indicator of the number of doses remaining.

Figure 3:
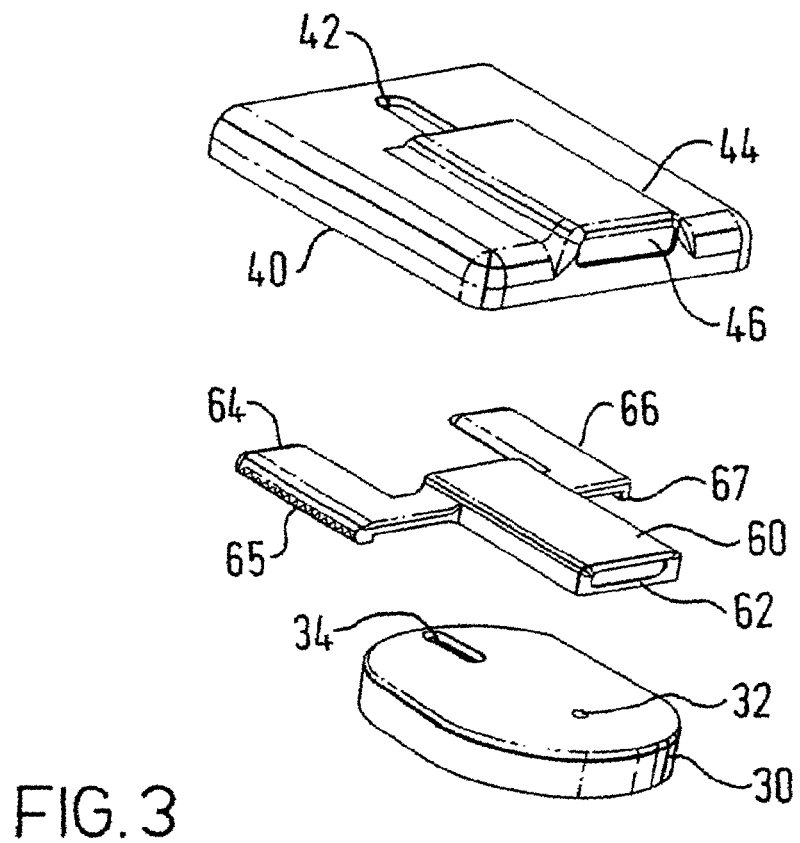
FIG. 3 is an exploded view of an inhalation device incorporating the cassette of FIG. 2.
Figure 3:
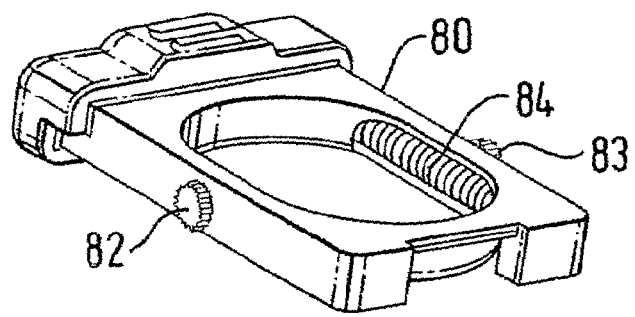
Figure 3:
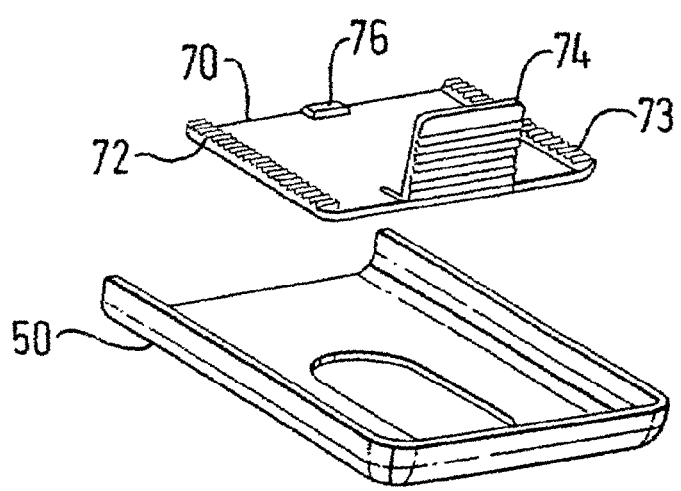

FIG. 3 shows an exploded view of an inhalation device incorporating the cassette of FIG. 2. The device may be seen to comprise an outer casing having first 40 and second 50 interlocking portions.

The first portion 40 is provided with a window 42, which is positioned, for registration with the window 34 on the cassette. The first portion 40 of the casing is also seen to have a raised part 44 provided with a generally rectangular opening 46 which is shaped for receipt of mouthpiece 60. The mouthpiece may be seen to have a housing defining an airway 62, which is of generally rectangular shape. The airway 62 is provided with an entrance hole (not shown) which, when the mouthpiece is in the in-use position, communicates with the exit hole 32 in the top cover of the cassette thereby allowing transfer of medicament from a cavity 14 in the disc 10 through to the airway 62. The housing is also provided with two arms 64, 66 having racks 65 thereon.

Figure 4A:
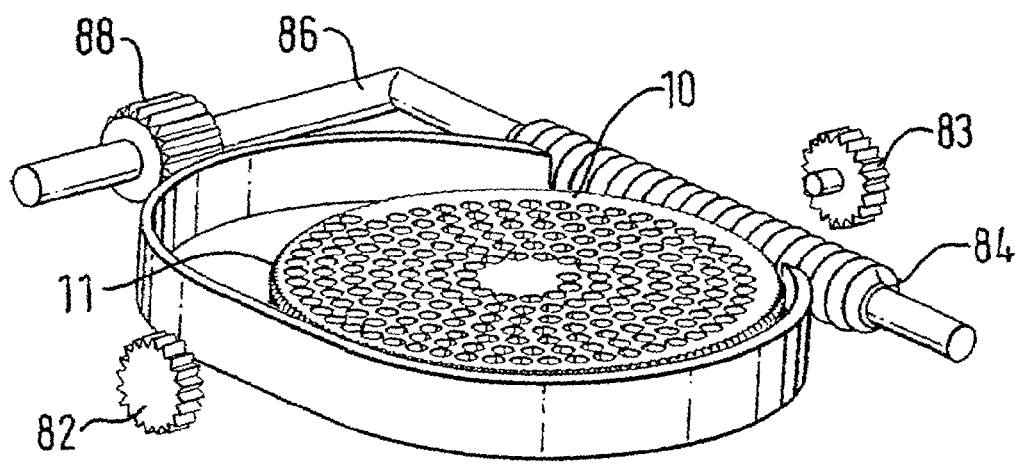
FIG. 4a is a simplified plan view of the drive system of the inhalation device of FIG. 3.

The second portion 50 of the casing is shaped for receipt of mouthpiece slider 70 (shown in more detail in FIG. 4a) which is slidably movable within the second portion 50 of the casing. The mouthpiece slider 70 is provided with racks 72, 73 which communicate via transfer wheels 82, 83 on the main body 80 (shown in more detail in FIG. 4b) with the racks 65, 67 on the arms 64, 66 of the mouthpiece 60. It may thus be seen that slidable movement of the mouthpiece slider 70 enables the mouthpiece 60 to be moved from a storage position within the casing to an in-use position in which it protrudes from the casing. The mouthpiece slider 70 is also provided with a hinged door 74 which may be seen to be movable from a closed position when the mouthpiece 60 is in the storage position to an open position as the mouthpiece 60 is moved to the in-use position.

Figure 4B:
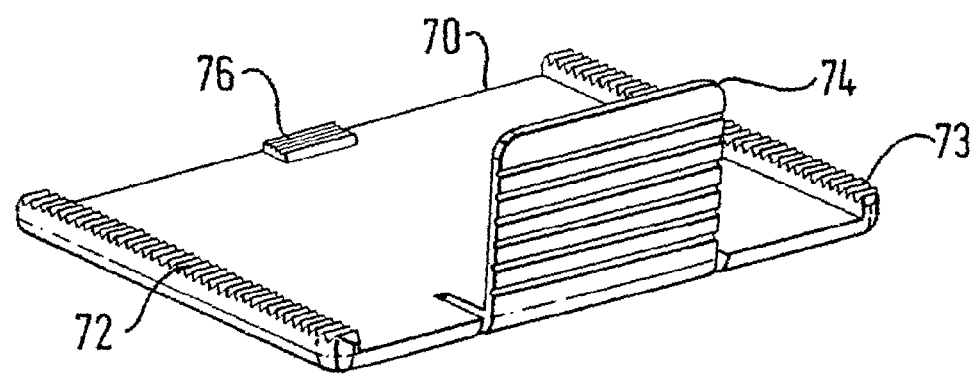
FIG. 4b is a simplified plan view of the mouthpiece slider of the inhalation device of FIG. 3.

The main body 80 may be seen to be shaped for receipt of the cassette and cartridge disc 10 contained therein. Referring to FIG. 4b, the main body includes a drive system for driving the rotation of the disc 10 within the cartridge. The drive system comprises an indexing screw 84, which communicates with the teeth 11 on the circumference of the disc 10 and with drive shaft 86. A fixed wheel 88 is provided to the central portion of the drive shaft 86. Rotation of the disc may be seen to be achievable by a user driven (e.g. by a thumb movement) rotation of the fixed wheel 88 and drive shaft 86 which causes rotation of the indexing screw 84 and hence rotation of the disc 10.

The fixed wheel 88 on the drive shaft 86 may also be seen to communicate with raised toothed portion 76 on the mouthpiece slider 70 such that the rotation of the fixed wheel 88 drives the slidable motion of the mouthpiece slider 70 and hence, translates into movement of the mouthpiece 60.

Figure 5:
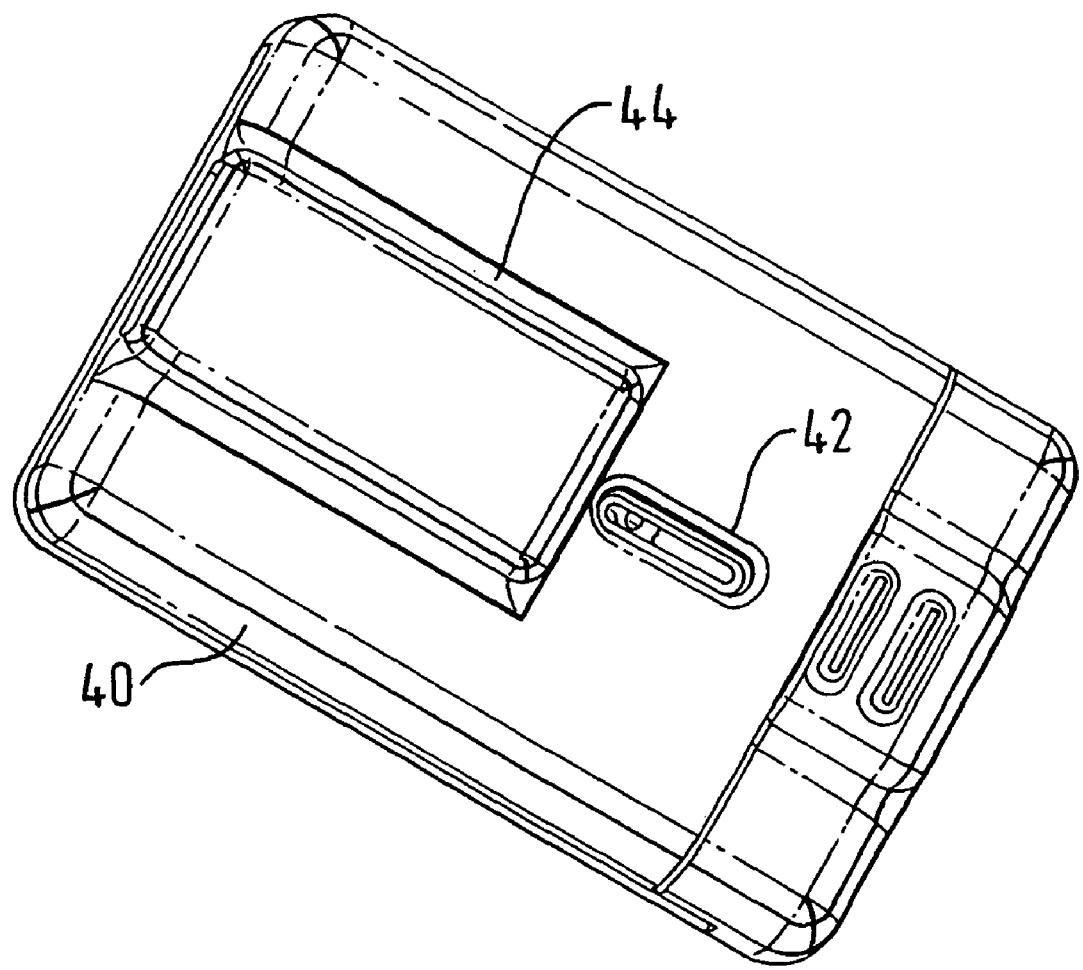
FIG. 5 is a plan view of the inhalation device of FIG. 3 in assembled form.

FIG. 5 shows a view of the inhalation device of FIG. 3. in assembled form with the mouthpiece 60 in the storage position. It may be seen that the window 42 enables the user to view the position of the disc 10 and hence, to gain information about the number of doses remaining.

It will be appreciated that variations of the cartridge, cassette and inhalation device of FIGS. 1a to 5 are possible. In particular, other drive systems for driving the rotation of the disc may be envisaged. The drive systems may be driven directly by the user or by electrically powered means. Inhalation devices having a fixed mouthpiece are envisaged.

In one variation (not shown) the tracking groove 18 in the reverse face 16 of the disc 10 is provided with indentations spaced at positions aligned with the positions of the medicament retaining cavities 14 on the top face 12 of the disc 10. The so-indented tracking groove 18 can thus function as a rack which may be driven by a suitably configured pinion drive to achieve the rotation of the disc 10.

Figure 6:
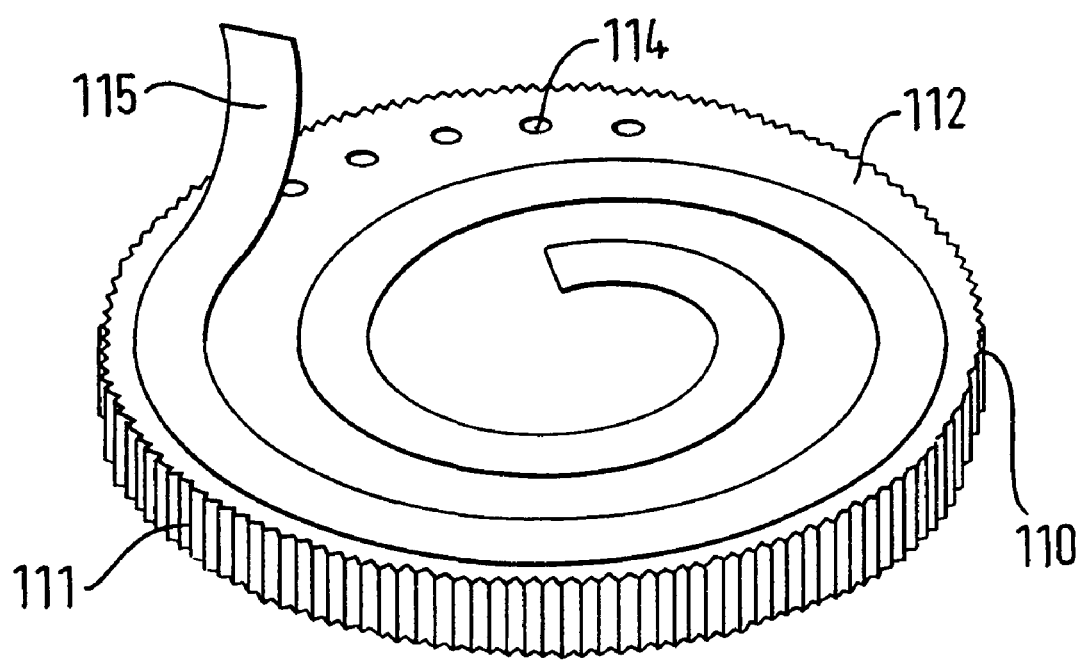
FIG. 6 is a view of the top of a second medicament cartridge in accord with the present invention.

FIG. 6 shows a second medicament cartridge in the form of a rigid disc 110 having teeth 111 on the circumference thereof. The top face 112 of the disc 110 is provided with a plurality of medicament retaining pockets 114 in a spiral path arrangement. A peelably removable sealing tape 115 is arranged along the spiral path. The tape 115 acts such as to seal the pockets 114. As shown, part of the sealing tape 115 has been drawn from the top face 112 of the rigid disc 110 to reveal some of the pockets 114 on the outermost part of the spiral. It may thus be appreciated that each pocket 114 on the spiral path is serially accessible (i.e. each in turn) by peelable removal of the tape 115.

When the second medicament cartridge is incorporated into an inhalation device, the free end of the sealing tape 115 is connected to an actuator. Peelable removal of the sealing tape 115 is achieved by movement of the actuator. Typically, the actuator is rotatable and rotation of the actuator results in coiling of the sealing tape 115 around the actuator. The actuator may be an axially mounted tapered pole.

Figure 7:
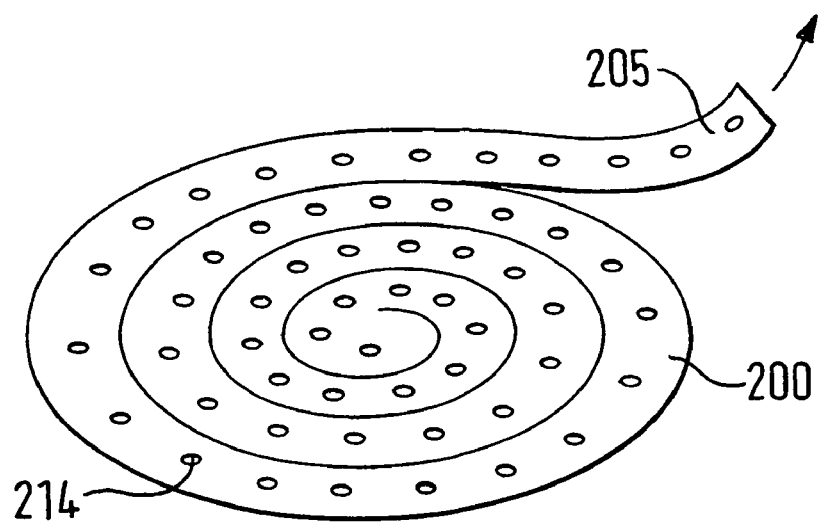
FIG. 7 is a view of a medicament carrier in accord with the present invention in the flat spiral storage configuration.

FIG. 7 shows a medicament carrier in the form of a tape 200 arranged in a flat spiral storage configuration. The tape 200 is provided with a plurality of medicament retaining cavities 214. The leading end 205 of the tape is shown extended from the storage configuration making it available for feeding into an access station of an inhalation device (not shown) where the medicament retainers 214 may be successively accessed. An airway will link the access station to a mouthpiece through which the patient inhales, thereby enabling inhalation of medicament.

Figure 8:
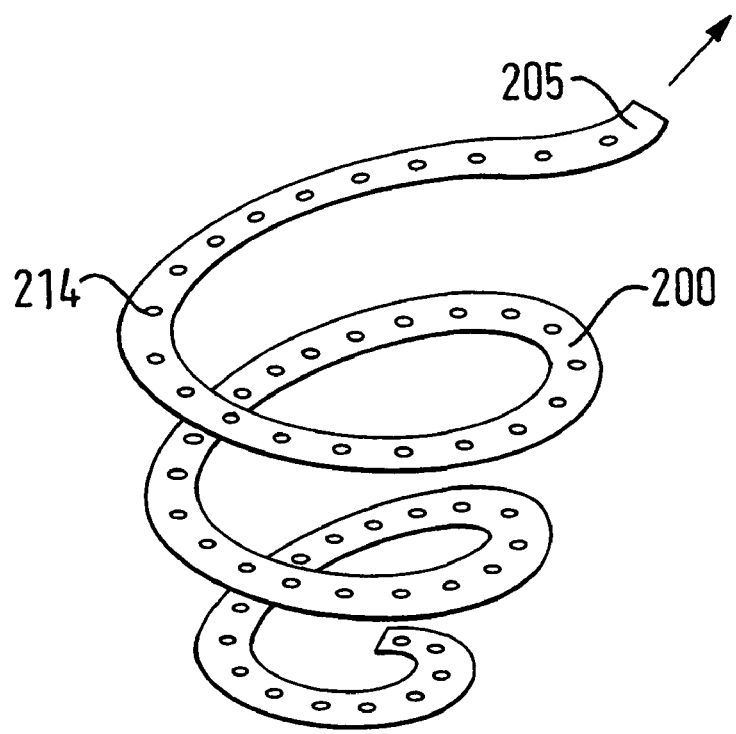
FIG. 8 is a view of the medicament carrier of FIG. 7 in the helically extended configuration.

FIG. 8. shows the medicament carrier tape of FIG. 7 with the tape 200 near fully expanded from the flat spiral storage configuration into a helical configuration.

Figure 9:
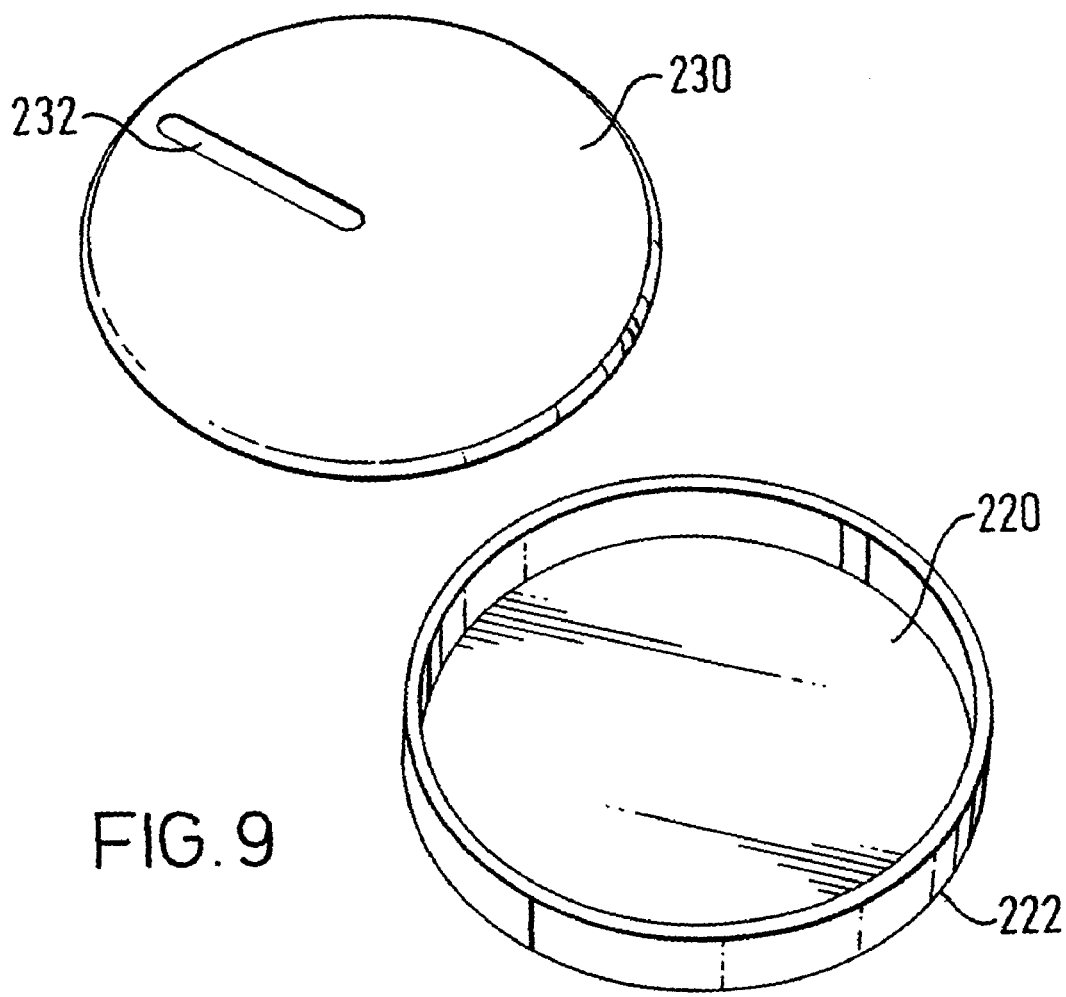
FIG. 9 is an exploded view of a medicament cartridge suitable for containing a medicament carrier of the type depicted in FIG. 7.

In one aspect, the tape 200 is housed in the storage configuration in a flat circular medicament cartridge, which is loadable into an inhalation device for dispensing therefrom. FIG. 9 shows an exploded view of a suitable flat circular cartridge having a bottom circular cover 220 with peripheral walls 222 extending therearound and a top cover 230. The top cover 230 of the cartridge is provided with an exit slit 232, which is sized and shaped to receive the leading end 205 of the tape 200.

Figure 10:
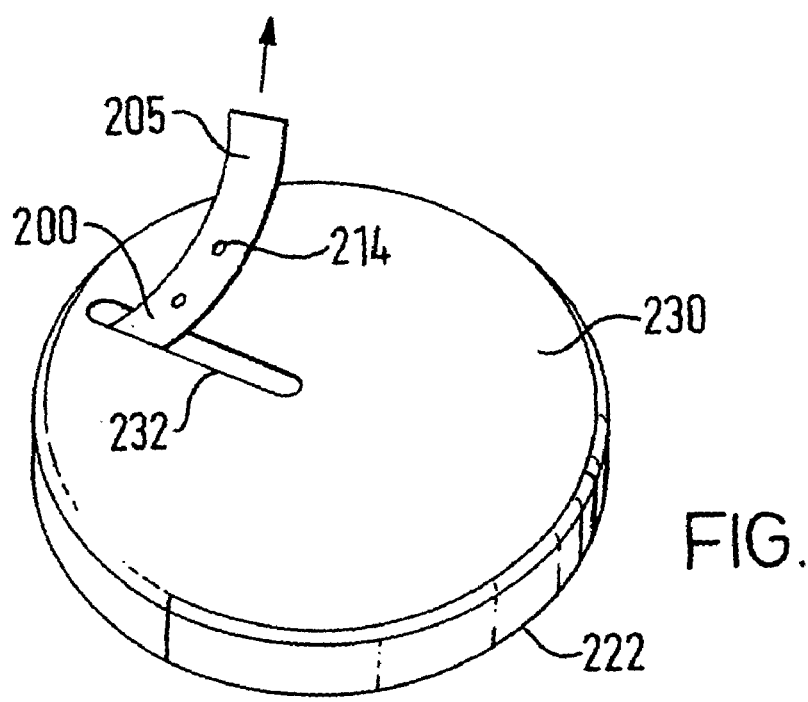
FIG. 10 is a view of the medicament cartridge of FIG. 9 in assembled form and loaded with a medicament carrier.

FIG. 10 shows the flat circular cartridge of FIG. 9 in assembled form and loaded with a medicament carrier tape. The leading end 205 of the tape protrudes from the exit slit 232 in the top cover 230 of the cartridge. When loaded into an inhalation device, the leading end 205 of the tape is progressively fed into a medicament access station to enable access to successive medicament retainers. The inhalation device will typically include a drive mechanism connected to the leading end 205 of the tape 200 to drivably encourage the tape towards the medicament access station. The drive mechanism may be manually actuable or it may be powered electrically.

The medicament carrier, cartridge and inhalation device herein is suitable for dispensing medicament, particularly for the treatment of respiratory disorders. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (-)-4-amino-3,5-dichloro-α-[[[6-[2-(2-pyridinyl)ethoxy]hexyl] methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclometasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an antiinflammatory steroid such as a beclomethasone ester (e.g., the dipropionate) or a fluticasone ester (e.g., the propionate).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

What is claimed is:

1. Inhalation device comprising
   a housing having an air inlet, an air outlet and an airway therebetween;
   a medicament carrier having a substantially planar first face and a plurality of medicament retainers defining openings in said first face, said openings being directed in a common direction and forming a single spiral path arrangement along said first face; and
   a mover for moving the medicament carrier relative to the housing so as to bring successive medicament retainers individually into communication with the airway.

2. Inhalation device according to claim 1, wherein said medicament carrier is a substantially rigid circular disk which is rotatable relative to the housing.

3. Inhalation device according to claim 2, wherein the circumference of said disk is provided with teeth and said teeth engage a worm drive for drivable rotation of said disk.

4. Inhalation device according to claim 2, wherein each medicament retainer comprises a pocket in a first face of the disk.

5. Inhalation device according to claim 4, wherein the disk defines a spiral track and said housing comprises a tracking pin, and said device is arranged such that said tracking pin extends into said spiral track, such that as the disk rotates relative to the housing said tracking pin moves along the spiral track and the disk moves translationally relative to the housing.

6. Inhalation device according to claim 1, wherein said air outlet is provided with a mouthpiece.

7. Inhalation device comprising
   a housing having an air inlet, an air outlet and an airway therebetween;
   a substantially planar medicament carrier plate having a generally flat upper surface, having a plurality of medicament retainers positioned along said flat upper surface, said retainers having openings in said upper surface, and said openings positioned in a single spiral path arrangement, each medicament retainer having a seal;
   an actuator for progressively unsealing each medicament retainer on the spiral path.

8. Inhalation device according to claim 7, additionally comprising a
   a mover for moving the medicament carrier relative to the housing so as to bring successive medicament retainers individually into communication with the airway.

9. Inhalation device according to claims 7, wherein each medicament retainer comprises a pocket.

10. Inhalation device according to claim 9, wherein said seal comprises a sealing tape arranged along said spiral path and wherein each pocket is serially accessible by peelable removal of the tape.

11. Inhalation device according to claim 10, wherein an end of said sealing tape connects to said actuator and peelable removal of the sealing tape is achievable by movement of the actuator.

12. Inhalation device according to claim 11, wherein said actuator is rotatable relative to the housing such that rotation of the actuator results in coiling of the tape around the actuator.

13. Inhalation device according to claim 12, wherein the actuator is an axially mounted tapered pole.

14. Inhalation device according to claim 7 wherein said actuator comprises a piercer for piercably unsealing a medicament retainer.

15. Inhalation device comprising
- a housing having an air inlet, an air outlet and an airway therebetween;
- an elongate carrier having a generally flat first surface, a plurality of medicament retainers positioned along the flat first surface, each retainer being defined by an opening in said flat first surface, wherein said elongate carrier is storable in a spiral configuration such that said openings are directed in a common direction; and
- a mover in communication with the elongate carrier for helically extending the elongate carrier such as to successively move each medicament retainer to an access position.

16. Inhalation device according to claim 15, wherein each medicament retainer comprises a cavity in the elongate carrier.

17. Inhalation device according to claim 16, wherein each medicament retainer has a seal, the device additionally comprising
- an actuator for unsealing a medicament retainer at the access position.

18. Inhalation device according to claim 17, wherein said seal comprises a sealing tape arranged along the elongate carrier and wherein each successive cavity is accessible by peelable removal of the tape from the elongate carrier.

19. Inhalation device according to claim 18, wherein an end of said sealing tape connects to said actuator and peelable removal of the sealing tape is achievable by movement of the actuator relative to the elongate carrier.

20. Inhalation device according to claim 19, wherein said mover is rotatable relative to the housing such that rotation of the mover results in coiling of the elongate carrier around the mover, and wherein said actuator is rotatable relative to the housing such that rotation of the actuator results in coiling of the tape around the actuator.

21. Inhalation device according to claim 20, wherein the mover is an axially mounted tapered pole and the actuator is also an axially mounted tapered pole.

22. Inhalation device comprising
- a housing having an air inlet, an air outlet and an airway therebetween;
- an elongate carrier having a plurality of doses thereon, wherein said elongate carrier is storable in a flat spiral configuration; and
- a mover in communication with the elongate carrier for helically extending the elongate carrier such as to serially move each dose to an access position.

* * * * *